United States Patent
Green

(10) Patent No.: US 8,840,847 B2
(45) Date of Patent: Sep. 23, 2014

(54) STERILANT SYSTEM

(75) Inventor: Bruce Philip Green, Northampton (GB)

(73) Assignee: Tristel PLC, Snailwell, Cambridgeshire (GB)

(*) Notice: Subject to any disclaimer, the term of this patent is extended or adjusted under 35 U.S.C. 154(b) by 1688 days.

(21) Appl. No.: 11/722,431

(22) PCT Filed: Jan. 27, 2006

(86) PCT No.: PCT/GB2006/000275
§ 371 (c)(1),
(2), (4) Date: Oct. 28, 2009

(87) PCT Pub. No.: WO2006/079822
PCT Pub. Date: Aug. 3, 2006

(65) Prior Publication Data
US 2010/0036305 A1    Feb. 11, 2010

(30) Foreign Application Priority Data
Jan. 28, 2005 (GB) .................................. 0501719.9

(51) Int. Cl.
| A61L 2/00 | (2006.01) |
| B67D 5/06 | (2006.01) |
| B65D 88/54 | (2006.01) |
| A01N 59/00 | (2006.01) |
| A61L 2/22 | (2006.01) |
| C01B 11/02 | (2006.01) |
| A01N 25/16 | (2006.01) |

(52) U.S. Cl.
CPC . *A61L 2/22* (2013.01); *A01N 59/00* (2013.01); *A61L 2/0082* (2013.01); *C01B 11/023* (2013.01); *A01N 25/16* (2013.01); *C01B 11/024* (2013.01)
USPC ........ 422/292; 222/190; 222/325; 222/402.1; 222/321.9

(58) Field of Classification Search
CPC ..... A01N 1/0215; A01N 25/16; A61K 8/046; A61L 2/00; B01F 17/00
USPC ................. 422/28, 292; 222/190, 325, 402.1, 222/321.9; 424/405, 53, 76.8; 252/186.1, 252/187.23
See application file for complete search history.

(56) References Cited

U.S. PATENT DOCUMENTS 5,337,929 A    8/1994    van der Heijden
(Continued)

FOREIGN PATENT DOCUMENTS

| EP | 0 081 017 A | 6/1983 |
| EP | 0 175 826 A1 | 4/1986 |
| EP | 0 423 817 A2 | 4/1991 |
| EP | 0 423 817 A3 | 4/1991 |
| GB | 2 404 337 A | 2/2005 |
| GB | 2 410 032 A | 7/2005 |
| JP | 11-229317 | 8/1999 |

(Continued)

OTHER PUBLICATIONS

Roberts et al., "Chlorine Dioxide for Reduction of Postharvest Pathogen Inoculum during Handling of Tree Fruits." *Applied and Environmental Microbiology*, vol. 60, No. 8(1994): 2864-2868. XP002384827.

*Primary Examiner* — Monzer R Chorbaji
(74) *Attorney, Agent, or Firm* — Merchant & Gould P.C.

(57) ABSTRACT

A two-part sterilant system comprises: (a) a first part comprising a first reagent in an aqueous medium having a first foam promoter dissolved therein and contained in a first dispenser whereby it may be dispensed as a first foam; and (b) a second part which comprises a second reagent in an aqueous medium having a second foam promoter dissolved therein and contained in a second dispenser whereby it may be dispensed as a second foam; wherein the first reagent and the second reagent will react to provide a sterilizing composition when the first foam is mixed with the second foam.

19 Claims, 2 Drawing Sheets

(56) References Cited

U.S. PATENT DOCUMENTS

| | | | |
|---|---|---|---|
| 5,696,046 A | 12/1997 | Green | |
| 6,007,772 A | 12/1999 | Green | |
| 6,520,377 B2 * | 2/2003 | Yquel | 222/1 |
| 2002/0122772 A1 * | 9/2002 | Lukenbach et al. | 424/44 |

FOREIGN PATENT DOCUMENTS

| | | | |
|---|---|---|---|
| JP | 11228317 | 8/1999 | |
| WO | WO 96/10916 | 4/1996 | |
| WO | WO 2004/032979 A2 * | 4/2004 | A61L 2/00 |
| WO | WO 2005/011756 A1 | 2/2005 | |

* cited by examiner

STERILANT SYSTEM

BACKGROUND OF THE INVENTION

1. Field of the Invention

The present invention relates to a sterilant system and method for sterilising surfaces.

2. Description of the Prior Art

Two-part sterilising solutions are used in applications where the active sterilising ingredient is unstable over time. The solution is therefore prepared in situ shortly before it is to be used. A particularly important sterilising agent is chlorine dioxide ($ClO_2$), which may be formed from mixtures of various reagents including: chlorite and acid; chlorate, peroxide and acid; and chlorite, hypochlorite, and a suitable buffer. Chlorine dioxide has excellent sterilising and bactericidal properties, and oral ingestion in man and animals has been shown to be relatively safe.

$ClO_2$ gas is a respiratory and eye irritant so its concentration in air needs to be controlled at safe levels. The occupational exposure standard limit (OES) in the UK is set at 0.3 ppm (0.9 mg/m$^3$) as a 15 minute short term exposure limit (STEL) and at 0.1 ppm for an 8 hour time-weighted average (TWA). In the USA, OSHA, NIOSH and ACGIH all set the limit at 0.1 ppm for long-term exposure.

$ClO_2$ sterilising solutions have many uses, particularly in hospital and medical environments where medical equipment and apparatus such as isolation tents need to be sterilised to reduce risks of cross-infection. The cleaning of endoscopes and other medical equipment with suitable chlorine dioxide solutions is known from earlier patents in the name of the present inventor, for example, European Patent Number 0 785 719 and U.S. Pat. Nos. 5,696,046 and 6,007,772, the contents of which are hereby incorporated by reference.

It is not always convenient to mix up batches of solutions for use in sterilising equipment. For wiping down (rather than thoroughly cleaning inside and out) of endoscopes and probes, wipes of alcohol, general-purpose detergent, or soapy water are generally used, but these are not as effective as chlorine dioxide. It is desirable to be able readily to make up small quantities of two-component sterilising agents when desired and to be able to make such agents up in a form in which they may be readily handled for a particular application and which is compatible with OES limits.

SUMMARY OF THE INVENTION

According to an aspect of the present invention there is provided a two-part sterilant system comprising:
(a) a first part comprising a first reagent in an aqueous medium having a first foam promoter dissolved therein and contained in a first dispenser whereby it may be dispensed as a first foam; and
(b) a second part which comprises a second reagent in an aqueous medium having a second foam promoter dissolved therein and contained in a second dispenser whereby it may be dispensed as a second foam;
  wherein the first reagent and the second reagent will react to provide a sterilising composition when the first foam is mixed with the second foam.

By dispensing each reagent in a foam the resulting sterilising composition provides good surface contact with minimal splashing. The foam may formulated to be tenacious and form-retaining so that it resists flow when applied to a vertical or sloping surface such as the plastic-walled tent of a hospital isolation unit.

Moreover, where the reagents react to produce a volatile sterilant, such as chlorine dioxide, we have found that the concentration of volatile sterilant in the air is reduced compared to a corresponding non-foamed mixture. This enables the use of higher concentrations of reagents than with a liquid system.

Because both reagents are dispensed in separate foams before they react together the reaction products are formed within the foam. This maximises retention of those products in the foam and on a surface to which they are applied, and minimises losses through evaporation.

The system may be used to sterilise medical apparatus and equipment, including sloping surfaces such as internal walls of isolation tents, or for sterilising hands of medical staff or patients to reduce the risk of cross-infection. The system may also be used to prepare sterilizing wound dressings, or for oral hygiene applications where reduction of bacteria within the oral cavity is desired. For this latter application the sterilising composition is preferably $ClO_2$, which may be used as a mouthwash, a breath freshener, or for gum treatment. Optional flavouring, fragrancing, or colouring agents may be included in the formulations. Typically, the sterilising foam composition will be applied via a toothbrush or other applicator, although it would be possible for a user to apply the foam directly to the oral cavity if desired.

The dispenser may be a conventional trigger-operated atomiser or foamer, or other manual pump foamer in which the contents are expelled manually by operation of the trigger by the user. Alternatively, the dispenser may contain a propellant to dispense the contents when operation of the trigger opens a valve, as is well known in applications such as shaving foam canisters and the like. Suitable dispensers will be well known to those skilled in the art. A foam dispenser may include a mixing chamber to facilitate mixing of the first part with air, for example as described in U.S. Pat. No. 5,337,929.

In a preferred embodiment, the first dispenser and the second dispenser are connected together or provided in a common housing. Preferably, the foams are dispensed simultaneously by operation of a single trigger or other actuator. A particularly preferred dispensing apparatus is the Dual Foamer supplied by Airspray International BV. The Dual Foamer consists of two pump systems, with one single actuator operating both chambers. It is a mechanical, non-aerosol foam dispenser which dispenses the two components as foams simultaneously in a precise and fixed ratio. The foams are kept separate until the moment of application. At that point, the ingredients combine to create an instant 50:50 foam formulation. The output is 0.8 ml of liquid as foam per stroke. The manufacturer claims that the foams are dispensed without drips, spills, blotches or leaks.

The dispensers preferably have a common outlet through which both foams are dispensed. This outlet may optionally be provided with an internal mixing chamber or a tortuous pathway which will promote mixing of the foams before they exit the common outlet.

The preferred sterilising agent is chlorine dioxide, which may be formed from suitable known reagents. In a preferred embodiment one reagent is a chlorite (notably sodium chlorite) and the other is an acid, preferably with a buffer. Suitable acids include lactic acid, citric acid, boric acid, phosphoric acid, acetic acid, sorbic acid, ascorbic acid, hydrochloric acid or mixtures thereof. In a preferred embodiment a mixture of acids is used, notably a mixture of citric, sorbic and boric acids.

A particularly preferred system is as described in EP 0 785 719, with the corrosion inhibitors optionally not included, and with other additives as desired for particular applications.

In addition to suitable indicators, optional additives may be selected from foam stabilisers, humectants, essential oils and fragrances. Other sterilising agents may also be employed; for example chlorine or oxygen. Chlorine may be produced by reaction between a hypochlorite such as sodium hypochlorite, and a suitable acid or buffer. Oxygen may be produced by reaction between a peroxide and a catalyst such as catalase, optionally in the presence of a buffer. For convenience hereinafter, the invention will be described with reference to chlorine dioxide as the sterilising agent.

Suitable foam promoters will be well known to those skilled in the art. Non-limiting examples include: sodium laureth sulphate, ammonium lauryl sulphate, cocamide DEA, cocamidopropyl betaine, sodium lauryl sarcosinate, cocamidopropylamine oxide, monoethanolamine lauryl sulphate, cocamidopropyl hydroxysultaine, cocoyl sarcosinate. Anionic, cationic, non-ionic and amphoteric surfactants may be employed depending on the chemistry of the reagents. The foam promoters are selected to provide a stable foam structure. The foam promoter may comprise from about 0.1 to 50% by weight of each part, notably from about 1 to 10%, preferably from about 3 to 6%.

Suitable foam stabilisers well known to those skilled in the art may also be used, in proportions similar to those for the foam-promoters. Non-limiting examples include: alkanolamides, for example monoethanolamides and diethanolamides, amine oxides, betaines, protein hydrolysates and cellulose derivatives such as carboxymethylcellulose.

To promote foam stability it is preferred that the first foam promoter is chemically compatible with the second foam promoter; for example it is preferred that both foam promoters are anionic or that both are cationic or that both are non-ionic. In a particularly preferred embodiment, the second foam promoter is the same as the first foam promoter.

In a preferred embodiment, a humectant is included in at least one of the first and second parts, preferably in both parts. Humectants serve to reduce the rate of evaporation of components and improve product feel if direct skin contact is involved. We have found that the use of a humectant reduces the volatility of chlorine dioxide, which reduces the odour of chlorine dioxide and prolongs the life of the activated mixture. Non-limiting examples of suitable humectants include sodium lactate and polyols, for example glycerine, sorbitol, propylene glycol, diethylene glycol and ethylene glycol. The humectant may be present in any desired amount, particularly from about 0.1 to 50% by weight, notably from about 0.5 to 10%, preferably from about 1 to 3%.

It will be understood that other solvents than water, for example ethanol or glycerol, may optionally be included in either or both of the first part and the second part providing that a sufficiently stable foam is produced.

The first and/or second part may further include a biocide to ensure that, in the event of poor mixing of the parts, a biocidal effect is still present. The first and/or second part may also include a preservative.

Equal weights of the first part and the second part may provide, when mixed, a sterilising composition having a pH of from 1.0 to 10.5, but it is preferred that the composition has a pH of from 4.5 to 6.5 as this may result in a more stable compound.

In a preferred embodiment, at least one of the first and second parts is provided with an indicator reagent that changes colour to show that sufficient mixing has taken place. Where the first part and the second part are of different pH, the indicator may be a pH-sensitive indicator. Suitable indicators are well known to those skilled in the art, non-limiting examples including: phenol red, litmus, thymol blue, pentamethoxy red, tropeolin OO, 2,4-dinitrophenol, methyl yellow, methyl orange, bromophenol blue, tetrabromophenol blue, alizarin sodium sulphonate, α-naphthyl red, p-ethoxychrysoidine, bromocresol green, methyl red, bromocresol purple, chlorophenyl red, bromothymol blue, p-nitrophenol, azolitmin, neutral red, rosalic acid, cresol red, α-naphtholphthalein, tropeolin OOO, phenolphthalein, α-naphtholbenzein, thymolphthalein, nile blue, alizarin yellow, diazo violet, tropeolin O, nitramine, Poirrer's blue, trinitrobenzoic acid, and mixtures thereof. It is preferred that the indicator is selected so that both parts are separately colourless and the colour develops when the two parts are mixed.

Alternatively, or additionally, one or more fluorescent additives may be included so that the mixture fluoresces to indicate mixing. Non-limiting examples of suitable fluorescing agents include: 4-methylumbelliferone, 3,6-dihydroxanthone, quinine, thioflavin, 1-napthol, harmine, coumarin, acridine orange, cotarmine, and mixtures thereof.

The indicator (colour change or fluorescent) may be included in either part. Preferred proportions by weight are about 0.1 to 10%, notably about 0.5 to 2%.

According to another aspect of the invention there is provided a method of sterilising a surface, comprising the steps of:
(a) preparing a quantity of a first foam from an aqueous medium containing a first reagent and a first foam promoter;
(b) preparing a quantity of a second foam from an aqueous medium containing a second reagent and a second foam promoter, the second reagent being capable of reacting with the first reagent to produce a sterilising composition;
(c) mixing the first foam and the second foam;
(d) applying the foams to a surface to be sterilised.

It will be understood that steps (a) and (b) may be carried out sequentially or simultaneously and that steps (c) and (d) may be carried sequentially in either order or simultaneously.

Preferably, equal volumes of each foam are applied.

In one embodiment, the sterilising composition is applied to a surface of a fabric to provide a sterilising wound dressing. In this embodiment, the sterilising composition preferably comprises $ClO_2$.

Other aspects and benefits of the invention will appear in the following specification, drawings and claims.

BRIEF DESCRIPTION OF THE DRAWINGS

The invention will now be further described, by way of example, with reference to the following drawings in which.

DETAILED DESCRIPTION

In this specification, all parts are by weight unless otherwise indicated.

Figure 1:
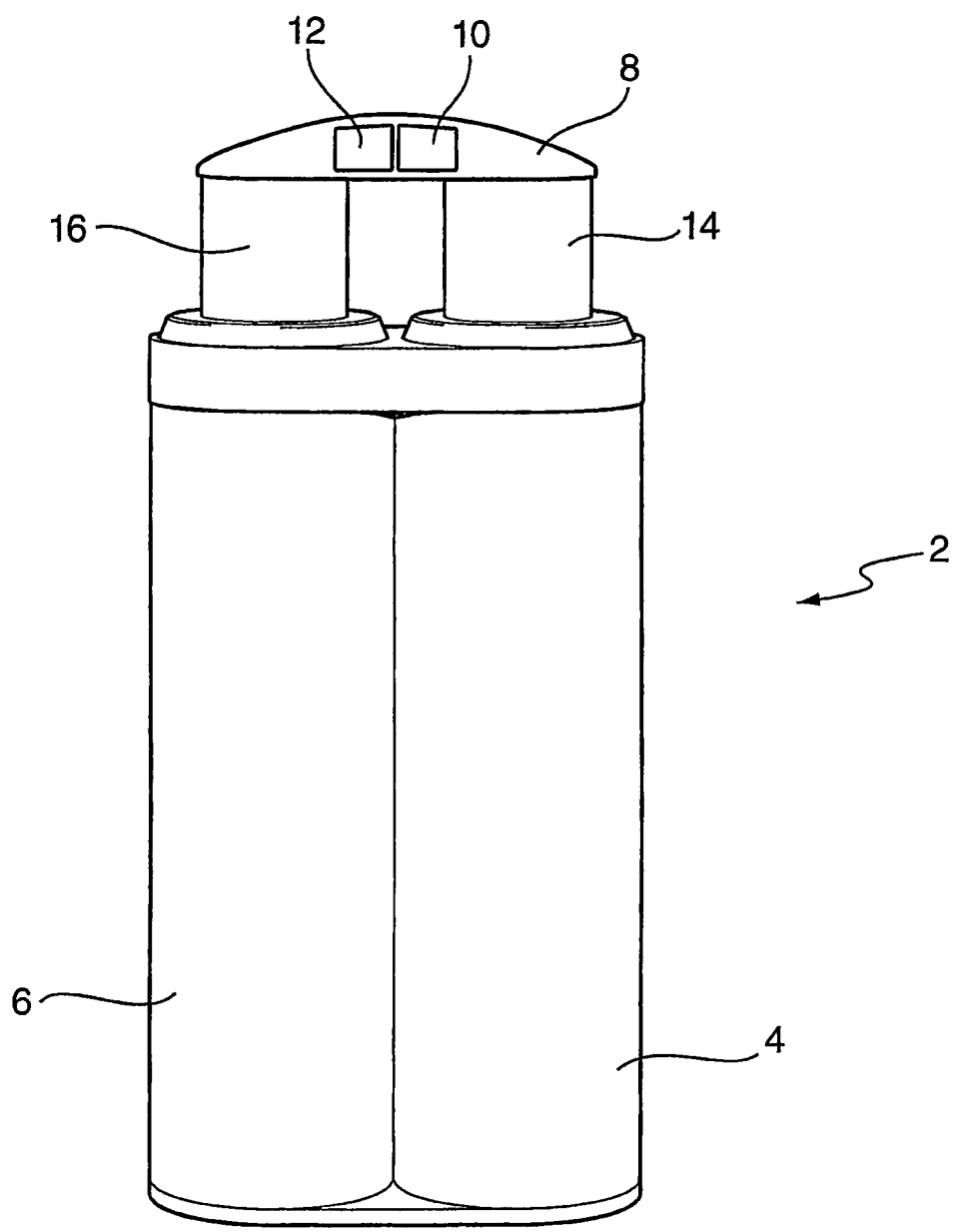
FIG. 1 shows a sterilant system in accordance with an embodiment of the present invention.

The Dual Foamer foam dispenser 2 shown in FIG. 1 (from Airspray International BV) has a first dispenser chamber 4 clipped to a second dispenser chamber 6. The chambers 4, 6 are part of two small foam pump systems which dispense their contents as foams when respective piston members 14, 16 are depressed. Operation of a single actuator 8 depresses both piston members 14, 16, causing a volume of liquid (in this example, 0.8 ml) to be pumped from each chamber 4, 6 simultaneously and combined with air to form a foam. The liquid from chamber 4 is turned into a first foam and the liquid from chamber 6 is turned into a second foam. The first and second foams are dispensed via respective separate nozzle orifices 10, 12 in the actuator 8.

In the present example, the first dispenser chamber 4 is filled with a liquid (first part) which comprises deionised water containing 0.75% of a first reagent (sodium chlorite), and 3.0% foam promoter (cocamidopropyl betaine).

The second dispenser chamber 6 is filled with an aqueous acid solution (second part). In this example, the acid solution comprises deionised water containing 0.5% citric acid, 0.05% sorbic acid, 0.05% boric acid, and 3.0% foam promoter (cocamidopropyl betaine). The solution also comprises 0.35% of a buffer (trisodium phosphate), 0.25% trisodium citrate, 1.0% glycerine, 0.1% benzotriazole, 0.1% sodium molybdate and 0.3% sodium nitrate.

The first part and the second part are miscible as liquids and as foams to produce $ClO_2$. However, they are kept separate from each other until each has been turned into a foam, thereby ensuring that $ClO_2$ is formed only within a foam and avoiding dispensing any liquid which may splash or trickle off a surface to be sterilised. We have found that the foam mixture provides effective surface sterilisation.

It is desirable that the $ClO_2$ is retained on a surface that is to be sterilised, and that airborne exposure to $ClO_2$ is kept at a safe level. Tests were carried out to measure $ClO_2$ concentrations in air for the first and second parts when mixed as liquids and when mixed as foams. The tests used the PiezOptic Personal Gas Dosimeter System, from PiezOptic Limited, Kent TN23 6NF, UK to measure $ClO_2$ concentrations in air. The Piezoptic system consists of small passive dosimeters (badges) which perform 5 identical tests simultaneously and which are read by a reader to provide a quantitative result. The badges are specified to monitor $ClO_2$ concentrations in the range 0.05-0.50 ppm.

Experimental Method

A test area of 60 mm×60 mm was marked out in a butler sink and a 250 ml flask was positioned on the edge of the test area.

Liquids 0.8 ml of the first part liquid was drawn into a first 1 ml syringe, and 0.8 ml of the second part liquid was drawn into another 1 ml syringe. The contents of both syringes were added to a 50 ml flask and left to react for 10 seconds. A sample of the mixture was poured onto the test area. Three PiezOptic badges were used. Badge No. 1 was positioned on the 250 ml flask at 25 mm above the mixture. Badge No. 2 was positioned 300 mm above the mixture, and Badge No. 3 was positioned 1000 mm above the mixture. The badges were left for the recommended time as per the manufacturer's instructions and $ClO_2$ air concentration results were recorded.

Foams

Using the Dual Foamer, two amounts of foam solution (1.6 ml) were pumped as foam into the test area. Badges were attached and positioned, and readings of $ClO_2$ concentration in air were taken using the same positioning and timing as for the liquids.

Results

Test results obtained from the badges for the liquids and foams are set out in Table 1.

TABLE 1

| Distance above mix. | Liquid | Foam |
| --- | --- | --- |
| 25 mm | >0.50 ppm | 0.50 ppm |
| 300 mm | 0.13 ppm | 0.05 ppm |
| 1000 mm | 0.09 ppm | 0.05 ppm |

In each case, the concentration of $ClO_2$ in air was reduced for the foam system, which will permit higher concentrations of reagents to be used within OES limits.

Figure 2:
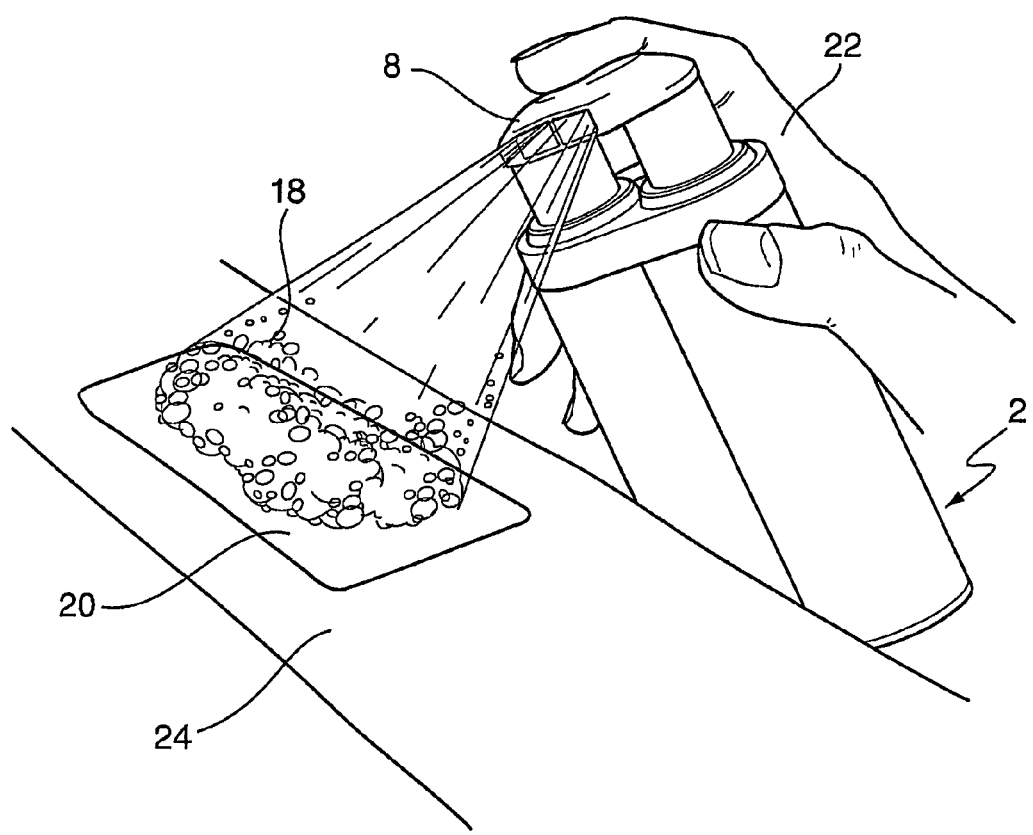
FIG. 2 shows the sterilant system of FIG. 1 being used to prepare a sterilising wound dressing.

Referring now to FIG. 2, the foam from each nozzle is sprayed onto a surface 20 by the action of a user's finger 22 on the actuator 8. The foams mix to provide a sterilising foam composition 18 containing $ClO_2$. In this example, the surface 20 is a surface of a fabric material, for example a gauze or bandage material, suitable for use as a wound dressing 24. The resulting wound dressing 24 may be used to dress any wound for which the use of a sterilising dressing is indicated, for example in the treatment of: burns, scalds, radiation therapy damage, cuts, abrasions, bed sores or ulcers. The wound dressing is of particular application in the dressing of leg ulcers. For wound dressing applications, antibiotics, antivirals, or other antimicrobial agents may optionally be incorporated in either or both of the first part and the second part. Suitable agents will be well known to those of ordinary skill in the art.

Typically, a wound to be treated will be wiped to remove any excess of exudate, and the wound dressing 24, carrying the sterilising foam composition 18, applied and held in place by suitable means, for example adhesive tape. In addition to promoting an antimicrobial environment, it is believed that the $ClO_2$ may help to break down and aid removal of biofilms and non-viable tissue, thereby promoting wound healing.

It is to be recognized that various alterations, modifications, and/or additions may be introduced into the constructions and arrangements of parts described above without departing from the ambit of the present invention as specified in the accompanying claims.

The invention claimed is:

1. A two-part sterilant system comprising:
    (a) a first part comprising a first reagent in an aqueous medium having a first foam promoter dissolved therein and contained in a first dispenser wherein the first dispenser is constructed to dispense the first part as a first foam; and
    (b) a second part which comprises a second reagent in an aqueous medium having a second foam promoter dissolved therein and contained in a second dispenser wherein the second dispenser is constructed to dispense the second part as a second foam;
        wherein the first reagent and the second reagent will react to provide a sterilising composition when the first foam is mixed with the second foam; and
        wherein the first dispenser and the second dispenser are connected together or provided in a common housing, and the first dispenser and the second dispenser have a common actuator, the actuation of which will cause the dispensers to dispense the first foam and the second foam simultaneously so that the first foam and the second foam are formed at the same time, and wherein the first dispenser and the second dispenser are constructed so that the first foam is formed in the first dispenser and the second foam is formed in the second dispenser and the first foam and the second foam are kept separate until dispensed from the first dispenser and the second dispenser.

2. A sterilant system according to claim 1, wherein at least one of the first part and the second part includes an indicator reagent that changes colour when the parts are mixed together.

3. A sterilant system according to claim 2, wherein the first part and the second part have a different pH and wherein the indicator reagent changes colour in response to a change in pH when the parts are mixed.

4. A sterilant system according to claim 1, wherein one of the first part and the second part contains sodium chlorite or sodium chlorate and the other comprises an acidic solution.

5. A sterilant system according to claim 4, wherein the acidic solution comprises a solution of citric acid, sorbic acid and boric acid.

6. A sterilant system according to claim 1, wherein the first foam promoter and the second foam promoter each comprise from 0.1 to 50% w/w of each of said first part and said second part.

7. A sterilant system according to claim 6, wherein the first foam promoter and the second foam promoter each comprise from 3 to 6% w/w of each of said first part and said second part.

8. A sterilant system according to claim 1, wherein at least one of the first part and the second part further comprises from 0.1 to 50% w/w of a humectant.

9. A sterilant system according to claim 8, wherein said humectant comprises from 1 to 3% w/w of said first part or said second part.

10. A sterilant system according to claim 1, wherein when equal weights of the first foam and the second foam are mixed they provide a sterilising composition having a pH of from 4.5 to 6.5.

11. A sterilant system according to claim 1, wherein each foam promoter is selected from the group comprising: sodium laureth sulphate, ammonium lauryl sulphate, cocamide DEA, cocamidopropyl betaine, sodium lauryl sarcosinate, cocamidopropylamine oxide, monoethanolamine lauryl sulphate, cocamidopropyl hydroxysultaine, cocoyl sarcosinate.

12. A sterilant system according to claim 1 wherein the first foam promoter is the same chemical or composition as the second foam promoter.

13. A sterilant system according to claim 1, wherein at least one of the first part and the second part further comprises a foam stabiliser selected from the group comprising: alkanolamides, amine oxides, betaines, protein hydrolysates, and cellulose derivatives.

14. A sterilant system according to claim 1, wherein the first reagent and the second reagent will react to form chlorine dioxide when the first foam is mixed with the second foam.

15. A sterilant system according to claim 1, further comprising a woven or non-woven fabric for receiving the first and second foams, suitable for use as a wound dressing.

16. A system according to claim 1, wherein the first dispenser and the second dispenser are constructed to provide that the first foam and the second foam are formed separately and subsequently mixed.

17. A wound dressing system comprising:
(a) a first part comprising a first reagent in an aqueous medium having a first foam promoter dissolved therein and contained in a first dispenser wherein the first dispenser is constructed to dispense the first part as a first foam; and
(b) a second part which comprises a second reagent in an aqueous medium having a second foam promoter dissolved therein and contained in a second dispenser wherein the second dispenser is constructed to dispense the second part as a second foam;
wherein the first reagent and the second reagent will react to provide a chlorine dioxide-containing sterilising composition when the first foam is mixed with the second foam; and wherein the first dispenser and the second dispenser are connected together or provided in a common housing, and the first dispenser and the second dispenser have a common actuator, the actuation of which will cause the dispensers to dispense the first foam and the second foam simultaneously so that the first foam and the second foam are formed at the same time, and wherein the first dispenser and the second dispenser are constructed so that the first foam is formed in the first dispenser and the second foam is formed in the second dispenser and the first foam and the second foam are kept separate until dispensed from the first dispenser and the second dispenser; and
(c) a woven or non-woven fabric for receiving the sterilising composition, for use as a sterile wound dressing.

18. A wound dressing system according to claim 17, wherein the first dispenser and the second dispenser are constructed to provide that the first foam and the second foam are formed separately and subsequently mixed.

19. A system for producing a sterilising foam for use in oral hygiene applications, the system comprising:
(a) a first part comprising a first reagent in an aqueous medium having a first foam promoter dissolved therein and contained in a first dispenser wherein the first dispenser is constructed to dispense the first part as a first foam; and
(b) a second part which comprises a second reagent in an aqueous medium having a second foam promoter dissolved therein and contained in a second dispenser wherein the second dispenser is constructed to dispense the second part as a second foam;
wherein the first reagent and the second reagent will react to provide a physiologically acceptable concentration of chlorine dioxide when the first foam is mixed with the second foam; and wherein the first dispenser and the second dispenser are connected together or provided in a common housing, and the first dispenser and the second dispenser have a common actuator, the actuation of which will cause the dispensers to dispense the first foam and the second foam simultaneously so that the first foam and the second foam are formed at the same time, and wherein the first dispenser and the second dispenser are constructed so that the first foam is formed in the first dispenser and the second foam is formed in the second dispenser and the first foam and the second foam are kept separate until dispensed from the first dispenser and the second dispenser.

* * * * *